US00PP09855P

United States Patent [19]

Rotolante

[11] Patent Number: Plant 9,855

[45] Date of Patent: Apr. 8, 1997

[54] ANTHURIUM 'ROTOLANTE NUMBER 2'

[75] Inventor: Denis W. Rotolante, Homestead, Fla.

[73] Assignee: Agri-Starts, Inc., Apopka, Fla.

[21] Appl. No.: 403,202

[22] Filed: Mar. 13, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Frank B. Robb; Robb & Robb

[57] ABSTRACT

An Anthurium cultivar of vigorous growth, continuously and profusely producing blooms from red buds and with bright, solid red, very long lasting petals which retain their color as the plant matures. The bloom is very long lasting and exhibits no discoloration until at least four weeks from cutting.

1 Drawing Sheet

GENERAL DESCRIPTION OF THE INVENTION

There is disclosed a new Anthurium plant of the *Anthurium andreanum* species resulting from a definite effort to produce an improvement in the species.

I discovered my new Anthurium plant by cross breeding the seed of the Anthurium known as 'Ruth Morat', U.S. Plant Pat. No. 8,540, with the pollen of the Anthurium known as 'Cultorum Small Red', unpatented, not publicly available, in an aseptic sterile laboratory environment in a nursery located near Apopka, Fla.

In the nursery, we produce substantial quantities of Anthurium and I have crossed certain varieties in an effort to produce new cultivars of varying forms, colors and characteristics. The plant of this disclosure was the result of such effort. This seedling was grown to maturity with siblings, retained for evaluation and testing and was found to produce highly desirable specimen plants when potted and to produce flowers in good quantity and suitable character for cutting for the florist industry. The spathe color of this plant was noted to be of excellent deep red color in pleasant contrast to the white spadix. Flowers were found to have exceptional lasting quality whether left to mature on the plant or taken as a cut flower. The strength of the long peduncle with the sizes, shapes and attitudes of the spathe and spadix make this plant ideally suited for the production of cut flowers of the highest quality.

I have caused my new plant to be asexually reproduced by tissue culture, and find that it comes true in successive generations which have been produced over time.

As will be understood from a consideration of the drawing, my new plant has some outstanding differences from known varieties. In particular, it is a vigorously growing plant, continuously and profusely producing blooms from red buds and with bright, solid red, very long lasting spathes which retain their color as the plant matures. The bloom is very long lasting and exhibits no discoloration until at least four weeks from cutting.

Thus I have disclosed unique characteristics which present a very different appearance from other Anthurium varieties or cultivars with which I am familiar.

Detailed characteristics of my plant are set forth hereinafter and where color is referred to as before and hereafter, The Royal Horticultural Society Colour Chart is used as a basis for comparison with the illustrations made by photographic process which is as nearly true as possible to make by such means.

It is particularly difficult to obtain illustrations of the darker colors displayed, but those shown are as nearly true as can be supplied.

BRIEF DESCRIPTION OF THE VIEWS OF THE DRAWINGS

The drawing is a close-up of the inflorescence of the plant and shows the top portions of mature leaves. The strong peduncle, a typical spathe and spadix is depicted in the center of the photographic drawing with the color; shape and relative sizes and coloration of these parts are illustrated.

BOTANICAL DESCRIPTION OF THE PLANT

Parentage:

*Seed parent.*—*Anthuriium andreanum* 'Ruth Morat' U.S. Plant Pat. No. 8,540.

*Pollen parent.*—*Anthurium andreanum.* 'Cultorum Small Red' unpatented.

Propagation: Plant tissue culture near Apopka, Fla.

Classification: *Anthurium andreanum* hybrid.

Plant description:

*Stem.*—Smooth, strong of medium size.

*Lenticles.*—Not obvious.

*Petioles.*—18–25 cm. Smooth, color green (143 C).

*Leaves.*—18–22 cm. long by 8–12 cm. wide, generally lanceloate with basal potions varying between truncate and obtuse, abundant, smooth texture and smooth edges, the upper side is smooth and green color (147 A), the under side is smooth and green color (147 B), short smooth stipules and ordinary ribs and veins.

*Bud.*—3–5 cm. long, pointed, red color (53 A); opening well.

*Flower.*—Type: Spathe and Spadix. Borne singly. Spathe: Cupped upon first opening the Spathe then flattens, shiny inside and outside with no pubescence; 3–5 cm. wide by 4–8 cm. long. Form — Oval and pointed. Color — Red (53 A) top and bottom. Texture — Thick and leathery.

*Peduncle.*—15–25 cm. long by 3–5 mm. wide. Green color (137 B). Smooth, stiff and nested in foliage.

Reproductive organs:

*Spadix.*—3–6 cm. long by 5–9 mm. wide., color (159 D)

*Flowering time.*—Continuous, once reaching blooming size which takes seven months from a 10 cm. tissue culture plug, under proper growing conditions.

*Disease.*—Initial greenhouse trials in Apopka, Fla. indicate good resistance against traditional diseases.

*Insects.*—No unusual susceptibility to insects noted to date.

GENERAL OBSERVATIONS

The plant grows as a bush exhibiting vigorous, compact growth with a height of 12–15 in. and a spread of 36 in. in a 10 in. pot.

I claim:

1. A new and distinct Anthurium plant substantially as herein shown and described, characterized particularly as to novelty by its vigorous growth, continuously and profusely producing blooms from red buds and with bright, solid red, very long lasting spathes which retain their color as the plant matures.

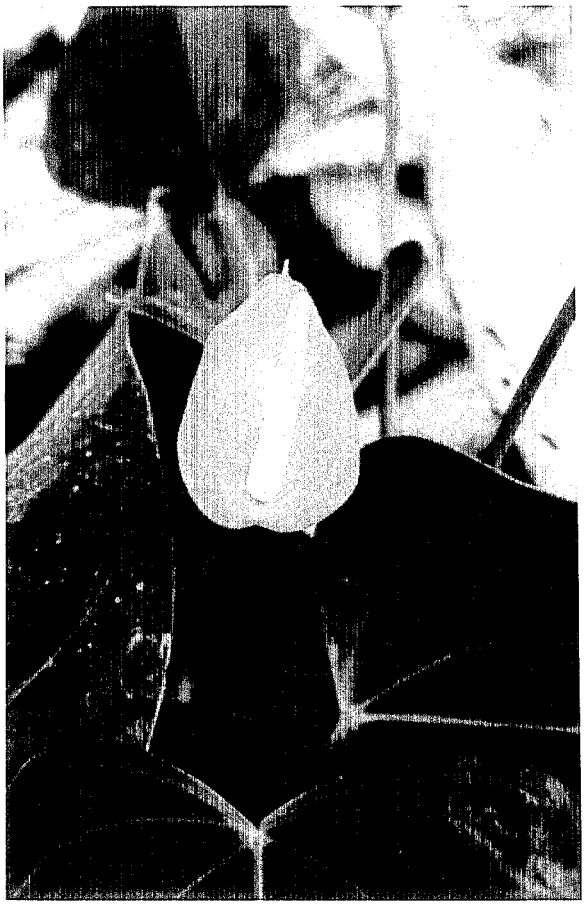

* * * * *